US00PP08126P

United States Patent [19]

Fruehwirth

[11] Patent Number: Plant 8,126

[45] Date of Patent: Feb. 2, 1993

[54] POINSETTIA PLANT NAMED C-27 WHITE

[75] Inventor: Franz Fruehwirth, Encinitas, Calif.

[73] Assignee: Paul Ecke Ranch, Inc., Encinitas, Calif.

[21] Appl. No.: 730,351

[22] Filed: Jul. 15, 1991

[51] Int. Cl.[5] ..... A01H 51/00

[52] U.S. Cl. ..... Plt./86.2

[58] Field of Search ..... Plt./86.1–86.4

[56] References Cited

U.S. PATENT DOCUMENTS

P.P. 7,235 5/1990 Fruehwirth ..... Plt. 86.1

*Primary Examiner*—James R. Feyrer

*Attorney, Agent, or Firm*—Arnold, White & Durkee

[57] ABSTRACT

This new Poinsettia is a stiff-stemmed, vigorous plant with large white, erect flower bracts. Cultivar 'C-27 White' is a sport of the red bracted 'C-27' (U.S. Plant Pat. No. 7,235). 'C-27 White', like its parent 'C-27', is unique because the flower bracts remain erect and do not droop, even after commercial shipping and handling or as the flowers mature. It always looks "fresh" which adds to its beauty and increases its value as a consumer product. Poinsettia 'C-27 White' has the same flowering response time and cultural requirements as its parent 'C-27'.

1 Drawing Sheet

BACKGROUND OF THE INVENTION

This new Poinsettia cultivar originated as a color sport of 'C-27' (U.S. Plant Pat. No. 7,235) in a greenhouse in Encinitas, Calif. It was selected from many plants because of its large, erect and white flower bracts and stiff stems, traits which distinguish it from other Poinsettia cultivars and seem to make it a desirable plant for commercial greenhouse production. After selection, vegetative reproduction of this plant was accomplished by stem cuttings for test purposes in Encinitas, Calif., and clones of the plant were subjected to successive generations of vegetative propagation which demonstrated that its distinct characteristics hold true from generation to generation.

DESCRIPTION OF THE PHOTOGRAPHS

Poinsettia 'C-27 White' is illustrated in the accompanying color photographs.

The upper photo is a side view of three unpinched 'C-27 White' plants in a 14 cm. pot.

The lower photo is a top view of the same plants showing flower and bract formation.

DESCRIPTION OF THE PLANT

The following is a detailed description of this new Poinsettia as observed in my greenhouse in Encinitas, Calif., during December, 1990. Flowering plants, grown as 3 unpinched plants per pot, were observed. The pot was 14 cm. in diameter and 11 cm. in height. Color designations were compared to the 1986 edition of R.H.S. Colour Chart, first published in 1966 by The Royal Horticultural Society, London, England.

THE PLANT

Origin: Sport of 'C-27' (U.S. Plant Pat. No. 7,235).

Classification:

*Botanic.*—*Euphorbia pulcherrima* Willd.

*Common name.*—Poinsettia.

*Cultivar name.*—'C-27 White'.

Form: Shrub.

Height: Medium.

Growth habit: As a single stemmed plant, upright and vigorous. The application of a chemical growth retardant may be needed to restrict height for commercial pot plant production. Observations of 3 plants in a pot with an overall height of 49 cm. and an overall width of 51 cm. were made. The bract diameter of individual flowers was 30 cm.

Branching: Poinsettia 'C-27 White', like its parent plant 'C-27', is not a self-branching cultivar. Branching can be enhanced by removal of the stem tip. Then, several flowering branches will develop on a single plant. Commercially, 'C-27 White' is valuable for those who wish to market single-stemmed plants with large, showy bracts. If pinched, one could expect 3–5 axillary branches to develop.

Growth rate: Very fast. Rooting of stem cuttings occurs in 12–18 days under intermittent mist. The plant will flower in about nine weeks under continuous long night conditions and night temperatures of about 16–18 degrees C.

Foliage: The foliage is clean and uniformly green from bottom to top of the plant. The leaves are of medium size, leaf blades typically being 10–11 cm. long and 8–9 cm. wide with leaf petioles 5–6 cm. long.

*Leaf shape.*—Typical leaves are ovate with acute bases and acuminate tips. Leaf margins are mostly entire with one or two slight indentations on each side of some leaf blades.

*Color.*—Upper side — Green, near RHS 147A. Under side — Green, near RHS 147B.

*Retention.*—The foliage lasts fairly well even under low light intensities in the consumer's home.

Bracts: Generally there are 18–24 white bracts of various sizes subtending the cyathia. The primary bracts have blades typically 14–15 cm. long and 10–11 cm. wide with petioles about 3 cm. long. Bract attitude is similar for both 'C-27 White' and its parent 'C-27'.

*Shape.*—Bracts are mostly ovate with acute bases and acuminate tips. Primary bracts are lobed with two indentations on either side of the bract. Secondary bracts are elliptic to obovate and have mostly entire margins.

*Color.*—Upper side — Creamy white, darker than RHS 155A, near RHS 4D. Under side — Creamy white, darker than RHS 155A, near RHS 4D.

Flowers: Generally, 18–24 cyathia (flowers) are present when the plant is in full bloom. Each cyathium is 6–7 mm long and 5 mm wide, green in color, and fringed with yellow at the distal end. One bright yellow nectar cup protrudes from the side of each cyathium. The flower pedicel is also green and about 5 mm in length. The stamens protruding from the cyathia are white.

What is claimed is:

1. A new and distinct Poinsettia cultivar, substantially as herein shown and described, characterized by its large white, erect flower bracts, and stiff stems.

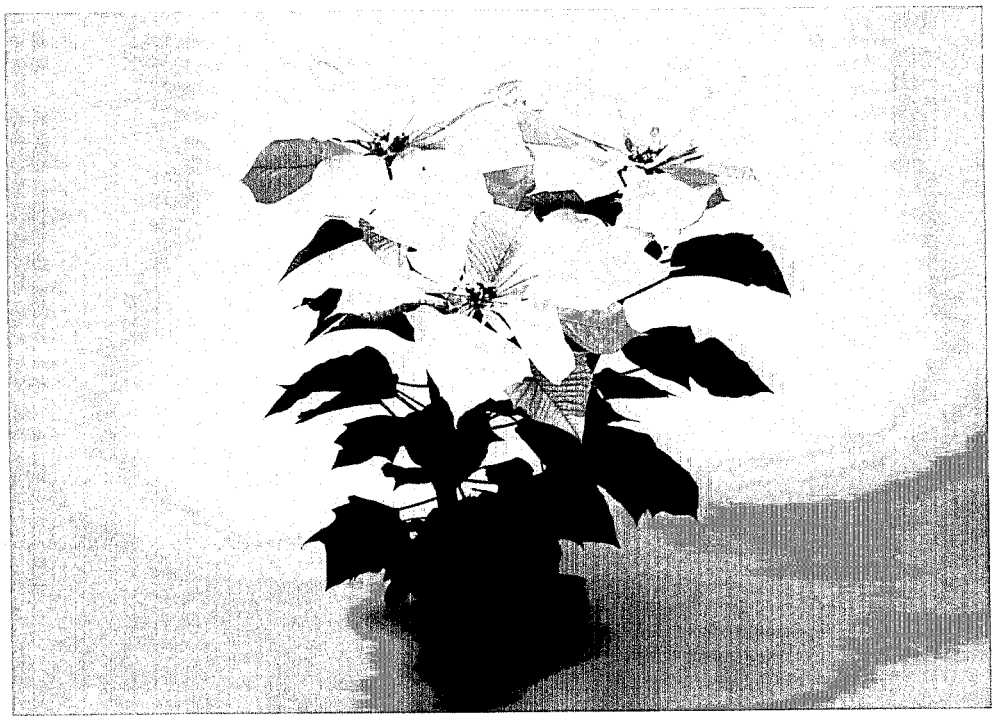
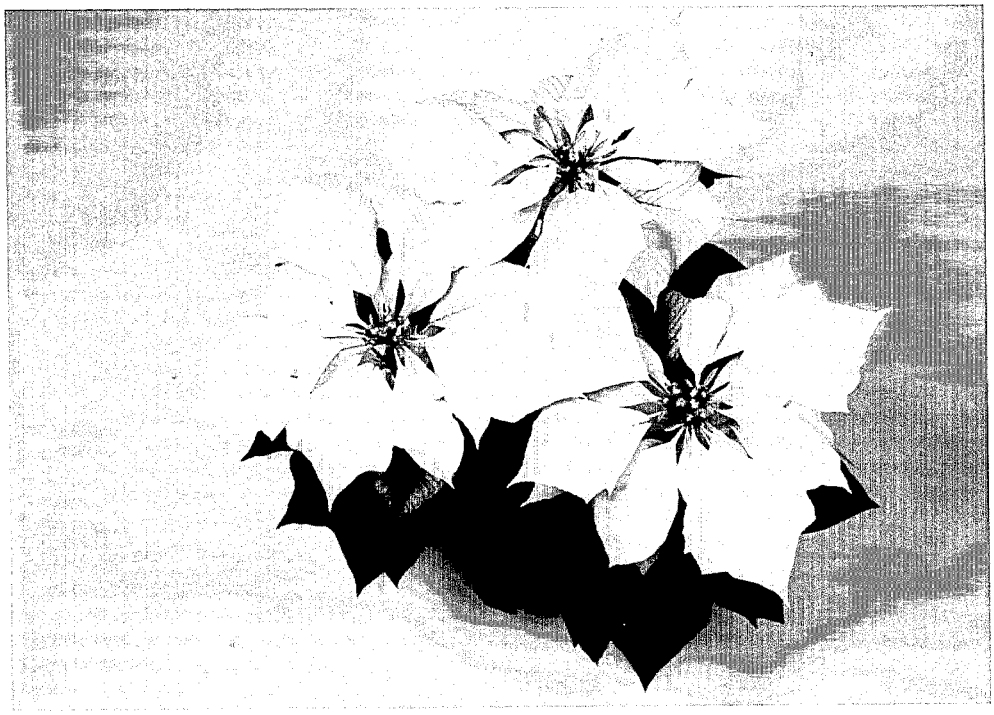

* * * * *